United States Patent
Lin et al.

(10) Patent No.: US 6,922,243 B2
(45) Date of Patent: Jul. 26, 2005

(54) METHOD OF INSPECTING GRAIN SIZE OF A POLYSILICON FILM

(75) Inventors: Kun-Chih Lin, Hsinchu (TW);
Long-Sheng Liao, Jungli (TW);
Chen-Chou Hsu, Taoyuan (TW)

(73) Assignee: Au Optronics Corp., Hsinchu (TW)

( * ) Notice: Subject to any disclaimer, the term of this patent is extended or adjusted under 35 U.S.C. 154(b) by 279 days.

(21) Appl. No.: 10/410,557

(22) Filed: Apr. 7, 2003

(65) Prior Publication Data

US 2004/0075835 A1 Apr. 22, 2004

(30) Foreign Application Priority Data

Oct. 21, 2002 (TW) .......................................... 91124254 A

(51) Int. Cl.⁷ ................................................. G01J 4/00
(52) U.S. Cl. ....................................................... 356/369
(58) Field of Search ................................ 356/369, 364; 250/559.09, 225; 438/7, 16

(56) References Cited

U.S. PATENT DOCUMENTS 6,128,084 A * 10/2000 Nanbu et al. ................ 356/369
2004/0092045 A1 * 5/2004 Bultman et al. .............. 438/16

* cited by examiner

*Primary Examiner*—Gregory J. Toatley, Jr.
*Assistant Examiner*—Roy M. Punnoose
(74) *Attorney, Agent, or Firm*—Ladas & Parry LLP

(57) ABSTRACT

A method of inspecting the grain size of a polysilicon film. A substrate covered by an amorphous silicon layer is provided. Next, the amorphous silicon layer is annealed by a laser beam with a predetermined laser energy density to transfer it to a polysilicon layer. Thereafter, the polysilicon layer is measured by a spectrometer under a predetermined photon energy range to achieve an optical parameter. Finally, the optical parameter is quantized to achieve a determining index, thereby monitoring the grain size of the polysilicon layer.

19 Claims, 3 Drawing Sheets

METHOD OF INSPECTING GRAIN SIZE OF A POLYSILICON FILM

BACKGROUND OF THE INVENTION

1. Field of the Invention

The invention relates to a method of inspecting a polycrystalline semiconductor film, and more particularly to a method of inspecting grain size of a polysilicon film.

2. Description of the Related Art

Currently, thin film transistor-liquid crystal display (TFT-LCD) technology mainly adopts two kinds of thin-film for fabricating transistors. One is amorphous silicon film, and the other is polysilicon film. The polysilicon thin film transistor (TFT) possesses the advantage of having electron mobility 10~100 times as high as that of amorphous silicon TFT. Therefore, there has been studied and developed a drive circuit integrated TFT-LCD using polysilicon TFT as a pixel switching element or a peripheral drive circuit for an LCD.

Polysilicon TFT is fabricated by a low temperature polysilicon (LTPS) process. In the LPTS technology, a polysilicon film is formed by performing excimer laser annealing (ELA) on an amorphous silicon film. Since the process temperature is below 600° C., this technology can be applied to a transparent glass substrate. In general, the electron mobility of polysilicon TFT is dependent on the grain size of a polysilicon film. That is, the electron mobility of polysilicon TFT is increased by increasing the grain size of a polysilicon film. In addition, the grain size of a polysilicon film is related to the laser energy density applied to the amorphous silicon film. Accordingly, it is necessary to measure the grain size of a polysilicon film, thereby determining an optimal laser energy density to control its grain size.

Conventionally, there is a well known method for observing the surface roughness of a polysilicon film using an optical microscope (OM) with a magnification of approximately 500~1000 to serve as a grain size index. However, since this method relies mainly on the human eye, the measured result is imprecise. Another conventional inspection method adopts a scanning electron microscope (SEM) to measure the grain size of a polysilicon film. This method, however, a destructive and excessive time is spent on sample fabrication and inspection, thereby decreasing throughput. In order to reduce the inspection time, use of an atomic force microscope (AFM) has been proposed. Although grain size can be observed and measured by AFM, approximately 30 minutes is required to observe and analyze one point of grain size. That is, AFM is unsuitable for analyzing multi-points.

Recently, use of an ellipsometer for measuring and use of effective medium approximation (EMA) or dispersion law for spectrum regression has been proposed. This method, however, cannot precisely obtain an optimal laser energy density and crystalline ratio, especially when the polysilicon film is formed by super lateral growth (SLG).

SUMMARY OF THE INVENTION

Accordingly, an object of the invention is to provide a novel method of inspecting the grain size of a polysilicon film that avoids the conventional off-line destructive inspection, precisely and quickly monitoring the grain size of a polysilicon film, thereby improving device properties and increasing throughput.

Another object of the invention is to provide a method of controlling grain size of a polysilicon film to determine the optimal laser energy density necessary for annealing, thereby controlling grain size of a polysilicon film.

Accordingly, a method of inspecting grain size of a polysilicon film is provided. First, a substrate covered by an amorphous silicon layer is provided. The amorphous silicon layer is annealed by a laser beam with a predetermined laser energy density to transfer it to a polysilicon layer. Thereafter, the polysilicon layer is measured by a spectrometer under a predetermined photon energy range to achieve an optical parameter. Finally, the optical parameter is quantized to achieve a determining index, thereby monitoring the grain size of the polysilicon layer.

According to another object of the invention, a method of controlling grain size of a polysilicon film is also provided. First, a first substrate covered by a first amorphous silicon layer is provided. The first amorphous silicon layer is annealed by a laser beam with different first predetermined laser energy densities to form a plurality of polysilicon regions therein. Next, each first polysilicon region is measured by a spectrometer under a predetermined photon energy range to achieve a plurality of optical parameters. Each optical parameter is quantized to achieve a plurality of first determining indices to determine a second predetermined laser energy density. Next, a second substrate covered by a second amorphous silicon layer is provided. The second amorphous silicon layer is annealed by the laser beam with the second predetermined laser energy density to transfer it to a polysilicon silicon layer having a controlled grain size.

The laser beam is an excimer laser beam. The first predetermined laser energy density is about 300~500 mJ/cm$^2$, and the second predetermined laser energy density means a laser energy density which meets the grain size specification of the polysilicon layer is provided.

Moreover, the spectrometer is a spectroscopic ellipsometer and the optical parameter is phase difference (cos Delta) or amplitude ratio (tan psi).

Moreover, the predetermined photon energy range is about 2.2~2.7 eV and 2.3~2.5 eV is preferred.

DESCRIPTION OF THE DRAWINGS

For a better understanding of the present invention, reference is made to a detailed description to be read in conjunction with the accompanying drawings, in which.

DETAILED DESCRIPTION OF THE INVENTION

Figure 1:
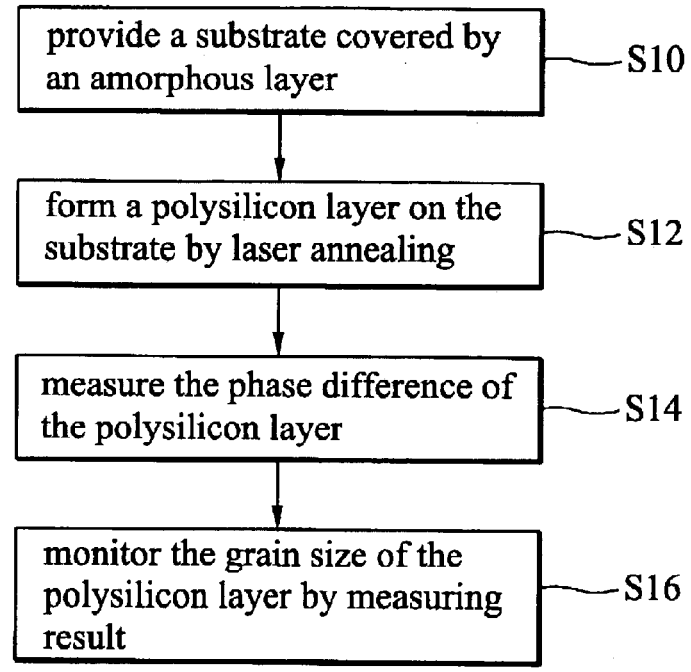
FIG. 1 is a flow diagram illustrating a method of inspecting grain size of a polysilicon film according to the invention.

FIG. 1 is a flow diagram illustrating a method of inspecting grain size of a polysilicon film according to the invention. First, in the step S10, a substrate, such as a transparent glass substrate, is provided. Moreover, an amorphous silicon layer is formed on the substrate. In this invention, the substrate is used for fabricating a thin film transistor-liquid crystal display (TFT-LCD) and the amorphous silicon layer is used for fabricating the channel layer of the TFT. The amorphous silicon layer has a thickness of about 300~1000Å and can be formed by conventional deposition, such as chemical vapor deposition (CVD).

Next, in the step S12, laser annealing with a predetermined laser energy density is performed on the amorphous silicon layer to transfer it to a polysilicon layer. In this invention, the laser beam for annealing can be an excimer laser beam with a laser energy density of about 300~500 $mJ/cm^2$.

Next, in the step S14, the polysilicon layer is measured by a spectrometer, such as a spectroscopic ellipsometer, to achieve an optical parameter. When a polarized light beam reflects from any specular surface, changes occur in both the amplitude and the phase of the oscillating parallel and perpendicular components of the electric field associated with the beam. The ellipsometer can measure the amplitude ratio (tan psi) of the reflected light polarized parallel (p-polarized light) and perpendicular (s-polarized light) and the phase difference (cos delta) between p- and s-components. In this invention, the optical parameter can be phase difference (cos delta) or amplitude ratio (tan psi).

Figure 2:
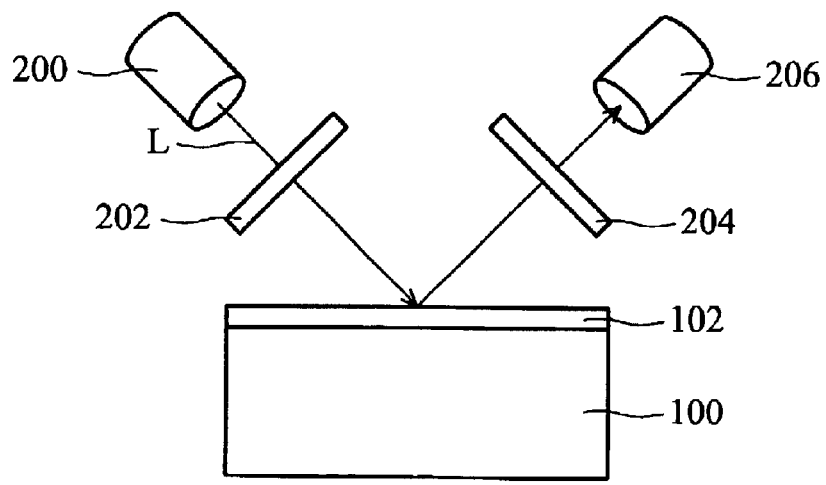
FIG. 2 is a schematic of an ellipsometer for inspecting a polysilicon film according to the invention.

FIG. 2 is a schematic of an ellipsometer for inspecting a polysilicon film according to the invention. In FIG. 2, a measuring light L is provided by a light source generator 200 and then forms a p-polarized light and an s-polarized light (not shown) through a polarizer 202 to project on the polysilicon layer 102 over the substrate 100. These polarized lights are reflected to the analyzer 204 and the detector 206 through the polysilicon layer 102. Thereafter, the optical parameter, such as phase difference or amplitude ratio, can be obtained via the analyzer 204 and the detector 206 under a predetermined photon energy range. In this invention, the predetermined photon energy range is about 2.2~2.7 eV. Preferably, the predetermined photon energy range is about 2.3~2.5 eV. The inventor discovers that the spectrums of the reflected polarized lights inspected by the ellipsometer under such predetermined photon energy range are changed distinctly to change the slope value of the phase difference (cos delta) curve when the polysilicon layer has a maximal grain size.

Finally, in the step S16, the grain size of the polysilicon layer is monitored by the measuring result of the ellipsometer. The optical parameter (phase difference (cos delta) curve) is quantized to achieve a determining index. For example, the slope value of the phase difference (cos delta) curve under a predetermined photon energy range, such as 2.3~2.5 eV, is calculated to serve as a determining index, which can determine whether the grain size of the polysilicon layer is out of specification, thereby monitoring the quality of the polysilicon layer. Since the inspection using ellipsometer does not destroy the substrate (non-destructive inspection), inspection time and fabrication cost can be reduced. Moreover, the ellipsometer can be easily integrated with the laser annealing system for in-line inspecting. That is, when the grain size of the polysilicon layer is out of specification, the inspection system immediately warns the operator, so the operator can check and promptly adjust the laser energy density, thereby maintaining optimal laser energy density to ensure quality. In addition, the laser annealing is part of the front-end of line (FEOL) process for the low temperature polysilicon (LTPS) process. Accordingly, if an abnormal product is found after inspection, it can be reworked or promptly abandoned right, thereby reducing the fabrication cost.

Figure 3:
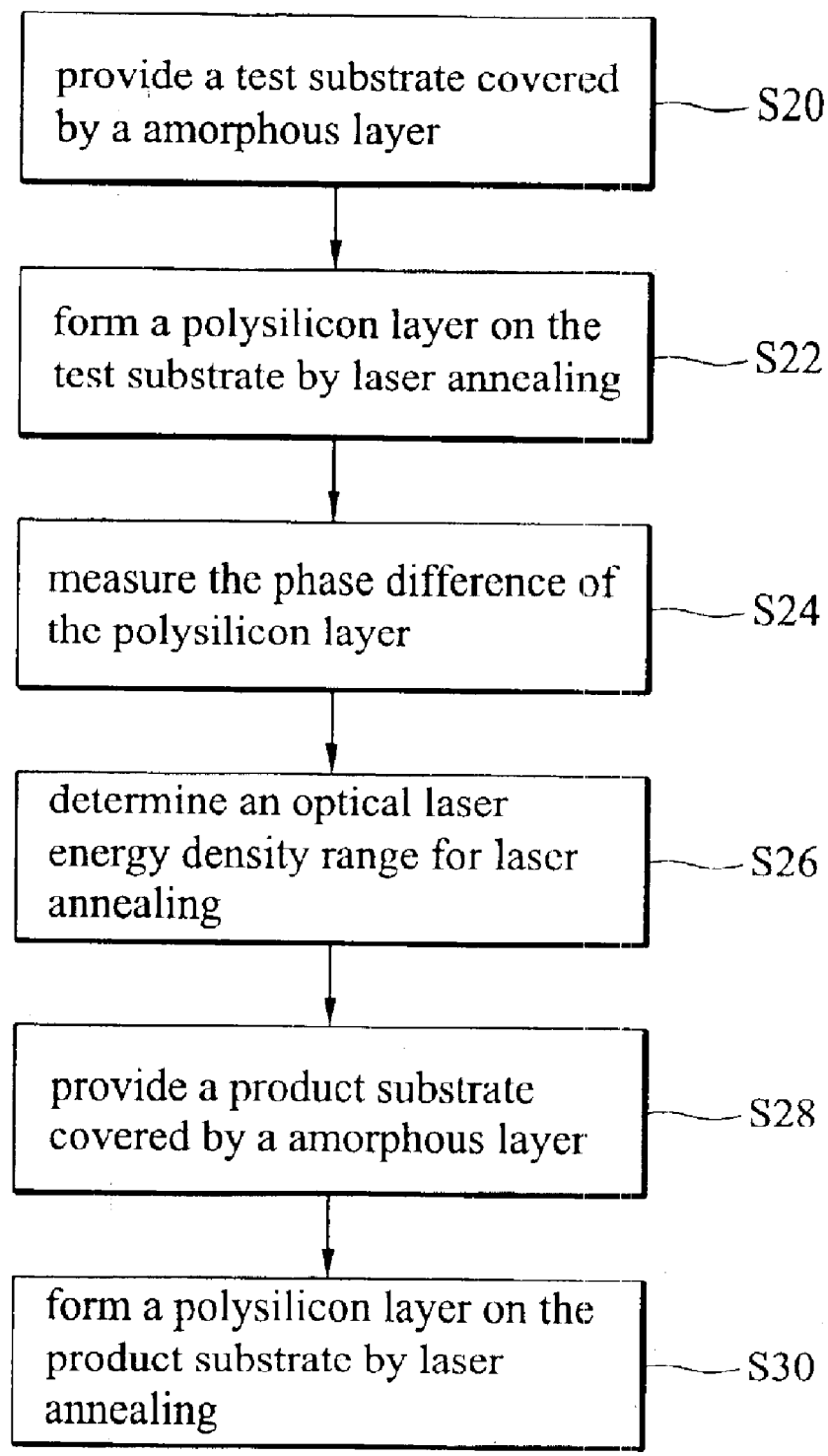
FIG. 3 is a flow diagram illustrating a method of controlling grain size of a polysilicon film according to the invention.

FIG. 3 is a flow diagram illustrating a method of controlling grain size of a polysilicon film according to the invention. First, in the step 20, a test substrate, such as a transparent glass substrate, is provided. Moreover, an amorphous silicon layer is formed on the test substrate. In this invention, the test substrate is used for pre-testing.

Next, in the step S22, laser annealing with different predetermined laser energy densities is performed on the amorphous silicon layer over the test substrate to form a plurality of polysilicon regions therein. In this invention, the laser beam for annealing can be an excimer laser beam with a laser energy density of about 300~500 $mJ/cm^2$.

Next, in the step S24, since the laser energy densities applied on the amorphous silicon layer over the test substrate vary, the grain sizes of the polysilicon regions over the test substrate also vary. These polysilicon regions are measured by a spectrometer under a predetermined photon energy range to achieve a plurality of optical parameters. In this invention, the spectrometer can be the spectroscopic ellipsometer, as shown in FIG. 2, and the optical parameters are phase difference (cos delta) or amplitude ratio (tan psi), as mentioned above. Moreover, the predetermined photon energy range is about 2.2~2.7 eV. Preferably, the predetermined photon energy range is about 2.3~2.5 eV.

For example, a test substrate having an amorphous silicon layer thereon is provided. Next, laser annealing is performed on the amorphous silicon layer under different predetermined laser energy densities A, B, C, D, and E selected from 300~500 $mJ/cm^2$ to form a plurality of polysilicon regions having different grain sizes therein. Next, the relationship between the phase difference (cos delta) and the photon energy (2.3~2.7 eV) of each polysilicon region is measured. The measuring result is shown in FIG. 4.

Figure 4:
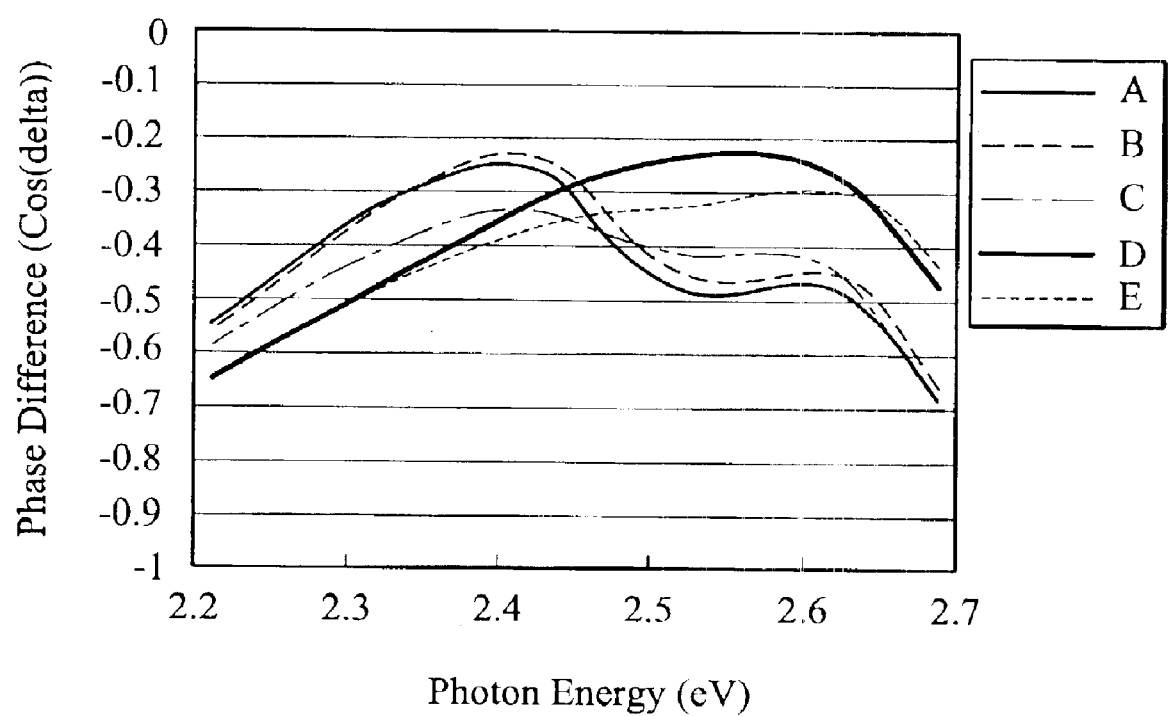
FIG. 4 is a graph showing the relationship between the phase difference (cos delta) and the photon energy (eV) according to the invention.

Next, in the step S26, a preferable laser energy density range for laser annealing is determined from the measured result shown in FIG. 4. The optical parameters (curves A, B, C, D, and E shown in FIG. 4) are quantized to achieve corresponding determining indices, thereby determining an optimal laser energy range. In this invention, these determining indices are obtained by calculating the slope values of these curves A, B, C, D, and E in the photon energy range of 2.3~2.5 eV. In FIG. 4, the slope values corresponding to the curves A, B, and C are apparently different with that corresponding to the curves D and E in the photon energy range of 2.3~2.5 eV. Here, the polysilicon regions formed by laser annealing using the predetermined laser energy density A, B, or C may be within grain size specification. On the contrary, the polysilicon regions formed by laser annealing using the predetermined laser energy density D or E is out of the grain size specification. That is, the optimal laser energy range is between the laser energy densities B and C, and the optimal laser energy is laser energy density A.

Next, in the step S28, a product substrate, such as a transparent glass substrate, is provided. Moreover, an amorphous silicon layer is formed on the product substrate. In this invention, the product substrate is used for fabricating TFT-LCD and the amorphous silicon layer is used for fabricating the channel layer of the TFT.

Finally, in the step S30, laser annealing with the optimal laser energy density A is performed on the amorphous silicon layer to transfer it to a polysilicon layer having a controlled grain size. Moreover, the steps S14 to S16 can proceed for in-line inspecting. Also, when the grain size of the polysilicon layer is out of specification, the inspection system immediately warns the operator, so the operator can check and promptly adjust the laser energy density, thereby maintaining the optimal laser energy density to ensure quality.

Compared with the prior art, the in-line inspection of the invention can precisely monitor the grain size of the polysilicon layer, thereby increasing throughput and yield. Moreover, since ellipsometer inspection is non-destructive inspection, inspection time and fabrication cost can be reduced.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of inspecting grain size of a polysilicon film, comprising the steps of:

providing a substrate covered by an amorphous silicon layer;

annealing the amorphous silicon layer by a laser beam with a predetermined laser energy density to transfer it to a polysilicon layer;

measuring the polysilicon layer by a spectrometer under a predetermined photon energy range to achieve an optical parameter; and quantizing the optical parameter to achieve a determining index to monitor the grain size of the polysilicon layer.

2. The method as claimed in claim 1, wherein the substrate is a glass substrate.

3. The method as claimed in claim 1, wherein the laser beam is an excimer laser beam.

4. The method as claimed in claim 3, wherein the predetermined laser energy density is about 300~500 mJ/cm$^2$.

5. The method as claimed in claim 1, wherein the spectrometer is a spectroscopic ellipsometer.

6. The method as claimed in claim 1, wherein the predetermined photon energy range is about 2.2~2.7 eV.

7. The method as claimed in claim 1, wherein the predetermined photon energy range is about 2.3~2.5 eV.

8. The method as claimed in claim 1, wherein the optical parameter is phase difference (cos Delta) or amplitude ratio (tan psi).

9. A method of controlling grain size of a polysilicon film, comprising the steps of:

providing a first substrate covered by a first amorphous silicon layer;

annealing the first amorphous silicon layer by a laser beam with different first predetermined laser energy densities to form a plurality of polysilicon regions therein;

measuring each first polysilicon region by a spectrometer under a predetermined photon energy range to achieve a plurality of first optical parameters;

quantizing each first optical parameter to achieve a plurality of first determining indices to determine a second predetermined laser energy density;

providing a second substrate covered by a second amorphous silicon layer;

annealing the second amorphous silicon layer by the laser beam with the second predetermined laser energy density to transfer it to a polysilicon silicon layer having a controlled grain size.

10. The method as claimed in claim 9, further comprising:

measuring the polysilicon layer by the spectrometer under the predetermined photon energy range to achieve a second optical parameter; and quantizing the second optical parameter to achieve a second determining index to monitor the grain size of the polysilicon layer.

11. The method as claimed in claim 10, wherein the second optical parameter is phase difference (cos Delta) or amplitude ratio (tan psi).

12. The method as claimed in claim 9, wherein the first and second substrates are glass substrates.

13. The method as claimed in claim 9, wherein the laser beam is an excimer laser beam.

14. The method as claimed in claim 13, wherein the first predetermined laser energy densities are about 300~500 mJ/cm$^2$.

15. The method as claimed in claim 9, wherein the spectrometer is a spectroscopic ellipsometer.

16. The method as claimed in claim 9, wherein the predetermined photon energy range is about 2.2~2.7 eV.

17. The method as claimed in claim 9, wherein the predetermined photon energy range is about 2.3~2.5 eV.

18. The method as claimed in claim 9, wherein the first optical parameter is phase difference (cos Delta) or amplitude ratio (tan psi).

19. The method as claimed in claim 9, wherein the second predetermined laser energy density is a laser energy density which can meet the grain size specification of the polysilicon layer.

* * * * *